Original
Class 47 Sub. 62
Sept. 27, 1955 | E. R. BARKER | Plant Pat. 1,422
APPLE TREE
Filed Dec. 1, 1954
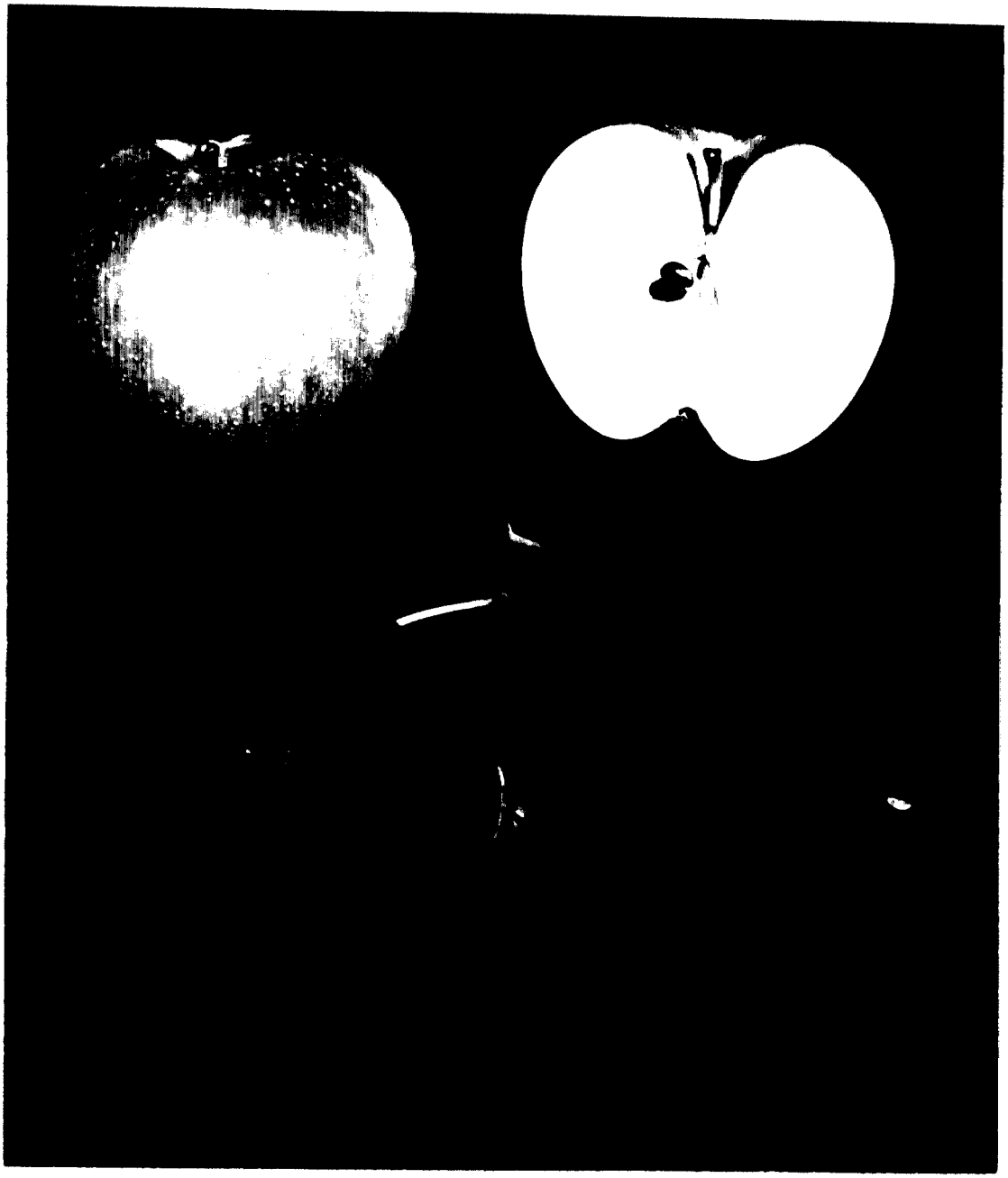
Inventor.
Elery R. Barker
By: Robb & Robb
Attorneys.

United States Patent Office

Plant Pat. 1,422
Patented Sept. 27, 1955

1,422

APPLE TREE

Elery R. Barker, Morgantown, W. Va., assignor, by mesne assignments, to Stark Bro's Nurseries and Orchards Company, Louisiana, Mo., a corporation of Missouri Application December 1, 1954, Serial No. 472,544

1 Claim. (Cl. 47—62)

The present invention relates to a new and distinct variety of apple tree which was discovered by me as a newly found seedling in my cultivated orchard on my farm in the Union District of Monongalia County, West Virginia. The particular parentage of my new variety is not definitely known to me, but I believe that the variety "Delicious" (unpatented) is one of the parents, as the fruit of my new variety more nearly resembles the fruit of "Delicious" than any other variety. Moreover, the new variety was discovered by me amongst trees of the variety "Delicious" which I was growing in my orchard, and from all the circumstances, it is quite likely that my new variety is a hybrid seedling or a seed mutation of "Delicious."

Although generally resembling the variety "Delicious," my new variety is definitely differentiated therefrom, as well as from all other varieties of which I am aware. One of the principal differences, which is highly valuable from a commercial standpoint, is the fact that the fruit of my new variety matures from 4 to 5 weeks earlier than that of "Delicious," although the season of bloom of both varieties is substantially the same. The flavor, color and shape of the fruit of my new variety generally resemble those of "Delicious," but the fruit of my new variety is broader, the apical protuberances are not as pronounced, the skin is slightly rougher, and the finish is not as bright, with the color a somewhat lighter and more striking hue of red, than the corresponding characteristics of "Delicious." In flavor, the fruit of my new variety is slightly more acid, and hence, superior for cooking purposes. When top-worked on "Delicious," the fruit of my new variety is larger than that of "Delicious."

With regard to the characteristics of the tree of my new variety, the crotch angles and distributions of fruiting wood are superior and better than those of "Delicious," and my new variety is a better annual bearer, and has leaves larger than those of "Delicious."

Asexual reproduction of my new variety by whip-grafting, as well as by top-working, as performed in Monongalia County, West Virginia, shows that the foregoing characteristics and distinctions come true to form and are established and transmitted through succeeding propagations.

The accompanying drawing shows typical specimens of the fruit and foliage of my new variety, with one of the fruit specimens in cross-section, as depicted in color as nearly true as it is reasonably possible to make the same in a color illustration of this character.

The following is a detailed description of my new variety, with color terminology in accordance with Ridgway's Color Standards and Nomenclature and with the Horticultural Color Guide, as indicated, except where general color terms of ordinary dictionary significance are obvious:

Observations made from specimens grown in Monongalia County, West Virginia.

Dates of first and last picking—August 10th–August 24th.

Tree: Medium size; vigorous; spreading; open; round-topped; rapid grower; hardy; productive; regular bearing.

Trunk: Medium stockiness; medium smoothness.

Branches: Medium thick; smooth; much-branched.
- *Color.*—Grey.
- *Lenticels.*—Few; medium size.

Leaves:
- *Size.*—Large. Length—from 4 inches to 5 inches. Width—from 2¼ inches to 3 inches.
- *Shape.*—Oval; abruptly pointed; medium thickness; smooth.
- *Margin.*—Coarsely serrate.
- *Color.*—Spinach Green, Plate o960, page 200, vol. 2 (Horticultural Color Guide).
- *Petiole.*—Medium length; medium thickness.

Flowers:
- *Dates of first and full bloom.*—April 10th–April 15th; medium early classification.
- *Size.*—Medium.
- *Color.*—White.

Fruit:
- *Maturity when described.*—Hard ripe; latter part of the month of August.
- *Size.*—Uniform. Axial diameter—2¾ inches. Transverse diameter—3 inches.
- *Shape.*—Conical; truncate at base and apex; ribbed.
- *Cavity.*—Symmetrical; abrupt at base; acute; undulate; pubescent toward apex. Depth—11/16 inch. Breadth—1 inch. Markings—Lavender Green, Plate ooo761/1, page 196, vol. 2 (Horticultural Color Guide) at apex.
- *Basin.*—Symmetrical; abrupt at base; wide flaring base; undulate; glabrous. Depth—5/16 inch. Breadth—⅞ inch. Markings—none.
- *Stem.*—Clubbed and medium stout; pubescent. Length—from ½ inch to ⅞ inch. Breadth—7/32 inch. Markings—Vinaceous Russet, Plate XXVII, Color No. 7″ (Ridgway).
- *Calyx.*—Open; segments persistent; narrowly lanceolate; separated at base; prostrate; reflexed from base at apex. Outer surface—pubescent. Inner surface—pubescent.
- *Eye.*—Large; open.
- *Skin.*—Thick; tough; smooth; glossy; waxed; with many, small, even, circular, conspicuous dots colored Pale Ochraceous Buff, Plate XV, Color No. 15′, Tone F (Ridgway), fairly uniformly distributed. Ground color—Citron Green, Plate 763, page 100, vol. 1 (Horticultural Color Guide). Color markings—Striped; blushed; self-colored; bright. Color—Blush of Scarlet, Plate 19/1, page 19, vol. 1 (Horticultural Color Guide), with stripes of Carmine, Plate 21, page 21, vol. 1 (Horticultural Color Guide).
- *Bloom.*—Wanting.
- *Scarfskin.*—Wanting.
- *General color effect.*—Bright red.
- *Flesh.*—Juicy. Color—satiny white, with greenish tint. Texture—firm; fine; from crisp to melting. Flavor—mild; rich. Aroma—distinct. Quality—best.
- *Core.*—Sessile. Bundle area—large; broadly cordate; unsymmetrical; acute at base; opposite and alternate with cell. Halves of core—unequal. Bundles—inconspicuous; one whorl. Color—Pod Green, Plate o61/2, page 120, vol. 2 (Horticultural Color Guide). Core lines—clasping; distinct in cross-section; small. Calyx tube—glabrous; cone-shaped. Entire depth—⅞ inch. Styles—wanting.

Stamens—in one distinct whorl; median. Axillary cavity—present. Seed cells—axile; open. Cell walls—approximate; thin; tough. Length—7/16 inch. Breadth—5/16 inch. Longitudinal section—oval; obtuse at apex. Surface—entire; smooth; narrow cross-section.

Seeds:

*Number.*—5 perfect; 3 imperfect; 2 per cell. Length 9/32 inch. Breadth—3/16 inch.

*Form.*—Obtuse.

*Color.*—Mars Brown, Plate XV, Color No. 13′, Tone M (Ridgway).

Use: Market; dessert; culinary.

Keeping quality: Good.

I claim:

A new and distinct variety of apple tree, substantially as herein described, characterized particularly as to novelty by its superior crotch angles and distribution of fruiting wood, and improved annual bearing habit, by its relatively large leaves and the early-maturing habit of its fruit, by the general similarity of its blooming season and the flavor, color and shape of its fruit to those of the variety "Delicious" (unpatented), but the fruit being distinguished from "Delicious" by being of broader dimension, having less pronounced apical protuberances, slightly rougher skin, duller finish but a lighter and more striking red general color tonality, slightly more acidity, and larger size when top-worked on "Delicious," substantially as herein shown and described.

No references cited.